United States Patent [19]

Imaki et al.

[11] Patent Number: 4,939,277

[45] Date of Patent: Jul. 3, 1990

[54] TETRAHYDROFURAN DERIVATIVES AND PROCESS FOR THEIR PRODUCTION

[75] Inventors: Naoshi Imaki, Atsugi; Isao Kawakami; Sinichiro Nakamura, both of Tokyo, Japan

[73] Assignee: Mitsubishi Kasei Corporation, Tokyo, Japan

[21] Appl. No.: 306,932

[22] Filed: Feb. 7, 1989

[51] Int. Cl.$^5$ .............................................. C07D 307/04
[52] U.S. Cl. ..................................................... 549/476
[58] Field of Search ......................................... 549/476

[56] References Cited

U.S. PATENT DOCUMENTS 2,572,566  1/9149  Himel et al. ........................ 549/476
2,920,081  1/1960  Privette et al. ..................... 549/476

OTHER PUBLICATIONS

A. Merz, Angew. Chem. Internat. Edit., "Phase–Transfer–Catalyzed Alkylation of Alcohols by Dimethyl Sulfate . . . " 12(10), pp. 846–847 (1973).

Shieh, J. Org. Chem., "Selective Alkylation and Aldol Reactions of (S)–(–)–13–hydroxy–δ–butyrolactone Diansor," 46(21), pp. 4319–4321, (1981).

J. McIntosh, J. Chem. Ed., "Phase–Transfer Catalysis Using Quaternary 'Onium salts," 55(12), pp. 235–238 (1978).

Helv. Chim. Acta 60 (2) 301–325, "Preparation of Auxilliaries for Asymmetric Syntheses from Tartaric Acid. Additions of Butyllithium to Aldehydes in Chiral Media", Dieter Seebach et al.

*Primary Examiner*—Glennon H. Hollrah
*Assistant Examiner*—Mark W. Russell
*Attorney, Agent, or Firm*—Oblon, Spivak, McClelland, Maier & Neustadt

[57] ABSTRACT

A tetrahydrofuran derivative of the formula:

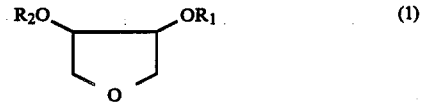

(1)

wherein each of $R_1$ and $R_2$ is an alkyl group having from 1 to 20 carbon atoms, and the two alkoxy groups $OR_1$ and $OR_2$ take a cis form to the plane of the tetrahydrofuran ring.

8 Claims, No Drawings

TETRAHYDROFURAN DERIVATIVES AND PROCESS FOR THEIR PRODUCTION

BACKGROUND OF THE INVENTION

1. Field of the Invention

The present invention relates to tetrahydrofuran derivatives and a process for their production. More particularly, it relates to tetrahydrofuran derivatives having a novel structure, which are useful as aprotic polar solvents or as starting materials for organic fine chemicals, and a process for their production.

2. Discussion of Background

As aprotic polar solvents having high dielectric constants, N-methyl-2-pyrrolidone, dimethyl acetamide and dimethyl sulfoxide have been known. However, these compounds contain hetero atoms such as nitrogen atoms or sulfur atoms, or reactive ketone groups. Therefore, their applications have been rather restricted.

On the other hand, as a compound having only ether linkages without containing nitrogen or sulfur atoms, (S,S)-(−)-3,4-dimethoxytetrahydrofuran has been known, wherein the two methoxy groups take a trans form to the plane of the tetrahydrofuran ring. This compound can be produced from (R,R)-(+)-2,3-dimethoxysuccinic acid ethyl ester, as disclosed in Helvetica Chemica Acta, vol. 60, p. 303 (1977), but the dielectric constant is not disclosed.

SUMMARY OF THE INVENTION

The present inventors have conducted researches for a compound having only ether linkages without containing nitrogen or sulfur atoms and having a high dielectric constant. It has been found that novel tetrahydrofuran derivatives having a certain specific geometric structure, have very high dielectric constants. The present invention has been accomplished on the basis of this discovery.

The present invention provides a tetrahydrofuran derivative of the formla:

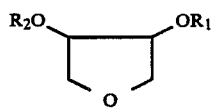         (1)

Wherein each of $R_1$ and $R_2$ is an alkyl group having from 1 to 20 carbon atoms, and the two alkoxy groups $OR_1$ and $OR_2$ take a cis form to the plane of the tetrahydrofuran ring, and a process for its production.

DETAILED DESCRIPTION OF THE PREFERRED EMBODIMENTS.

The novel tetrahydrofuran derivatives of the present invention represented by the formula 1 include, for example, cis-3,4-dimethoxytetrahydrofuran, cis-3,4-diethoxytetrahydrofuran, cis-3,4-dipropyloxytetrahydrofuran, cis-3,4-dioctyloxytetrahydrofuran, (±)-3-ethoxy-4-methoxytetrahydrofuran, cis-3,4-didodecyloxytetrahydrofuran and cis-3,4-dioctadecyloxytetrahydrofuran.

These tetrahydrofuran derivatives of the present invention can be prepared by the following process.

Firstly, erythritol of the formula:

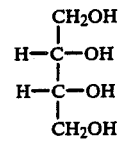         (2)

is subjected to cyclodehydration to form a cis-3,4-dihydroxytetrahydrofuran of the formula:

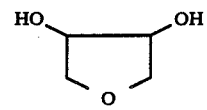         (3)

wherein the two hydroxyl groups take a cis form to the plane of the tetrahydrofuran ring.

The cyclodehydration reaction of erythritol is conducted by a method per se known, for example, by heating under reflux a mixture comprising erythritol, water and concentrated sulfuric acid. After the reaction, sulfuric acid is removed by an anion exchange resin, and the product is extracted with a suitable solvent to obtain the compound of the formula 3 substantially in a quantitative yield.

Cis-3,4-dihydroxytetrahydrofuran of the formula 3 thus obtained, is then reacted with an alkali metal compound to convert it to the corresponding alkali metal salt, which is then reacted with an alkylating agent having from 1 to 20 carbon atoms in an inert solvent such as dry ethyl ether, dry tetrahydrofuran, dioxane, dimethylformamide or N-methylpyrrolidone, to obtain a tetrahydrofuran derivative of the formula 1.

The alkali metal compound includes, for example, sodium metal, potassium metal, lithium metal, sodium hydride, sodium methoxide and sodium ethoxide, and it is used in an amount of at least one equivalent per equivalent of the hydroxyl group of the compound of the formula 3.

Cis-3,4-dihydroxytetrahydrofuran is reacted with an aqueous alkaline solution and an alkylating agent having from 1 to 20 carbon atoms in the presence of an interphase transfer catalyst, whereby a tetrahydrofuran derivative of the formula 1 is obtained.

As the interphase transfer catalyst, an alkyl ammonium such as tetrabutylammonium bromide or trioctylmethylammonium chloride may be used. As the aqueous alkaline solution, a highly concentrated aqueous solution of sodium hydroxide or potassium hydroxide can be used.

As a solvent, a poor solvent such as hexane is usually employed. However, no solvent may be used.

As the alkylating agent, a well-known alkyl halide or dialkyl sulfuric acid ester having from 1 to 20 carbon atoms may be employed. Specifically, an alkyl halide such as methyl iodide, ethyl iodide, octyl iodide, methyl bromide, ethyl bromide, propyl bromide, methyl chloride, ethyl chloride, octyl chloride or dodecyl chloride, or a dialkyl sulfuric acid ester such as dimethyl sulfate, diethyl sulfate, dipropyl sulfate or dibutyl sulfate, may be employed. Such an alkylating agent is used usually in an amount within a range of from 0.2 to 20 mols per mol of the compound of the formula 3.

The alkylating reaction is conducted usually within a range of from −78° to 200°. After completion of the reaction, treatments such as hydrolysis, neutralization and extraction, are conducted to obtain the desired tetrahydrofuran derivative.

Now, the present invention will be described in further detail with reference to Examples. However, it should be understood that the present invention is by no means restricted to such specific Examples.

EXAMPLE 1

Preparation of cis-3,4-dimethoxytetrahydrofuran (1) Preparation of cis-3,4-dihydroxytetrahydrofuran To 20 g of 50% sulfuric acid, 10 g of erythritol was added, and the mixture was heated and reacted under reflux for 15 hours. Then, the reaction solution was diluted by an addition of 40 ml of water, and then sulfuric acid was removed by passing the solution through a column (5 cm×50 cm) of an anion exchange resin (Diaion SA-20, manufactured by Mitsubishi Kasei Corporation). Then, the solution was concentrated, and the syrup thereby obtained was subjected to extraction treatment with chloroform for 10 hours by means of a Soxhlet extractor. The extract solution was concentrated, and the residue was distilled to obtain 3.5 g of cis-3,4-dihydroxytetrahydrofuran having a boiling point of from 86°–88° C./0.1 mmHg.

(2) Preparation of cis-3,4-dimethoxytetrahydrofuran 200 ml of hexane was added and dispersed to 28.8 g (0.6 mol) of sodium hydride (50% dispersion in oil), and the dispersion was left to stand. Then, the supernatant was removed, and 200 ml of dry tetrahydrofuran (THF) was added and dispersed again. The supernatant was removed, and 600 ml of dry THF was added and substituted for hexane.

Then, after cooling the dispersion with ice to a temperature of from 0° to 5° C., 31.23 g (0.3 mol) of cis-3,4-dihydroxytetrahydrofuran obtained in the above step (1) and 77.95 g (0.62 mol) of dimethyl sulfate were gradually dropwise added over a period of one hour. After the dropwise addition, the reaction system was maintained at a temperature of from 5° to 10° C. for 3 hours, and the reaction was further continued under stirring at a temperature of from 20° to 30° C. for 3 hours.

After completion of the reaction, by-product sodium monomethyl sulfate in a gel state was separated by filtration, and THF was removed from the filtrate. The residue was distilled to obtain 24 g of cis-3,4-dimethoxytetrahydrofuran having a boiling point of from 92° to 95° C.

The $^1$H-NMR and $^{13}$C-NMR data and the results of the elemental analysis of this substance were as follows:

| $^1$H-NMR(CDCl$_3$ solvent) | | | |
|---|---|---|---|
| δ(ppm): | 3.44 | s | 6H (—O—CH$_3$) |
|  | 3.60 | m | 6H (—CH$_2$—, —CH—) |
|  | 3.96 | | |
| $^{13}$C-NMR(CDCl$_3$ solvent) | | | |
| δ(ppm): | 57.9 | | (—O—CH$_3$) |
|  | 70.4 | | (CH$_2$—) |
|  | 80.8 | | (—CH—) |

| Elemental analysis: | C | H | O |
|---|---|---|---|
| Calculated (%) | 54.53 | 9.15 | 36.32 |
| Measured (%) | 54.29 | 9.35 | 36.36 |

EXAMPLE 2

48 g (1 mol) of sodium hydride (50% dispersion in oil) was dispered in 250 ml of hexane, and the supernatant was removed. Then, 250 ml of dry THF was added and dispersed again, and the supernatant was removed. Then, 250 ml of dry THF was again added to substitute for hexane.

Then, the dispersion was cooled to 0° C., and then a solution prepared by dissolving 52 g (0.5 mol) of cis-3,4-dihydroxytetrahydrofuran obtained in step (1) of Example 1 in 75 ml of dry THF, was dropwise added thereto. Six hours later, 149.2 g (1 mol) of methyl iodide was further dropwise added, and the mixture was reacted at room temperature for 3 days under stirring.

After completion of the reaction, by-product sodium iodide was removed by filtration, and the filtrate was concentrated. The residue was distilled to obtain 30.0 g of cis-3,4-dimethoxytetrahydrofuran as identified in Table 1.

The dielectric constant (relative permitivity) of cis-3,4-dimethoxytetrahydrofuran obtained in Example 1 was measured. The results are as follows:

Measuring device: YHP-Automatic Capacitance Bridge 4270A
Cell: Dielectric cell for liquid
Temperature and humidity for measurement: 25° C., 50% RH
Results for measurement:

|  | Cis form (present invention) ε' | Trans form ε' |
|---|---|---|
| 10$^3$ Hz | 54.6 | — |
| 10$^4$ Hz | 54.6 | — |
| 10$^5$ Hz | 30.4 | 20.0 |
| 10$^6$ Hz | 30.3 | — |

EXAMPLE 3

10.4 g of cis-3,4-dihydroxytetrahydrofuran and 80 g of a 50% sodium hydroxide aqueous solution were mixed. Then, 38.3 ml of octyl bromide and 400 mg of trioctylmethylammonium chloride as an interphase transfer catalyst, were added thereto. The reaction was conducted at 80° C. for 16 hours. After cooling, the product was extracted with hexane, dried and distilled to obtain 16.0 g of a product having a boiling point of from 147° to 151° C./0.2 mmHg. This product was found to be cis-3,4-dioctyloxytetrahydrofuran from the $^1$H-NMR.

$^1$H-NMR data are as follows:

| $^1$H-NMR (CDCl$_3$ solvent) | | | |
|---|---|---|---|
| δ(ppm) | | | Integrated value |
| 0.85–0.91 | triplet | CH$_3$ | 6 |
| 1.27 | multi | —CH$_2$— | 20 |
| 1.54–1.64 | multi | —O—C—CH$_2$— | 4 |
| 3.42–3.58 | multi | —O—CH$_2$—C | 4 |
| 3.75–3.83 | multi |  | 2 |

| $^1$H-NMR (CDCl$_3$ solvent) δ(ppm) | | Integrated value |
|---|---|---|
| 3.89–3.96 | multi 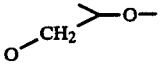 | 4 |

EXAMPLE 4

0.5 g of cis-3,4-dihydroxytetrahydrofuran was dissolved in 4 ml of dimethylformamide. Then, 390 mg of sodium hydride (50% dispersion in oil) was added thereto to obtain an alkali salt. After maintaining it at 50° C. for one hour, 2.1 ml of octyl bromide was added thereto. The mixture was reacted at 55° C. for 18 hours.

The reaction was terminated by an addition of water, and the product was extracted with hexane, dried and purified by column chromatography to obtain 0.82 g of cis-3,4-dioctyloxytetrahydrofuran. This product had the same NMR date as obtained in Example 3.

The tetrahydrofuran derivatives of the present invention exhibited very high dielectric constants and thus are useful as solvents for capacitor or electric cells, or as aprotic polar solvents for chemical reactions.

What is claimed is:

1. A tetrahydrofuran derivative of the formula:

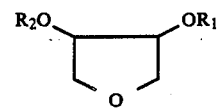 (1)

wherein each of $R_1$ and $R_2$ is an alkyl group having from 1 to 20 carbon atoms, and the two alkoxy groups $OR_1$ and $OR_2$ take a cis form to the plane of the tetrahydrofuran ring.

2. The tetrahydrofuran derivative according to claim 1, which is cis-3,4-dimethoxytetrahydrofuran.

3. The tetrahydrofuran derivative according to claim 1, which is cis-3,4-diethoxytetrahydrofuran.

4. The tetrahydrofuran derivative according to claim 1, which is cis-3,4-dipropyloxytetrahydrofuran.

5. The tetrahydrofuran derivative according to claim 1, which is cis-3,4-dioctyloxytetrahydrofuran.

6. The tetrahydrofuran derivative according to claim 1, which is (±)-3-ethoxy-4-methoxytetrahydrofuran.

7. The tetrahydrofuran derivative according to claim 1, which is cis-3,4-didodecyloxytetrahydrofuran.

8. The tetrahydrofuran derivative according to claim 1, which is cis-3,4-dioctadecyloxytetrahydrofuran.

* * * * *